United States Patent [19]

Frantzen

[11] Patent Number: 5,769,866
[45] Date of Patent: Jun. 23, 1998

[54] INCISION DEVICE

[75] Inventor: John J. Frantzen, Copperopolis, Calif.

[73] Assignee: Global Therapeutics, Inc., Broomfield, Colo.

[21] Appl. No.: 856,363

[22] Filed: May 14, 1997

[51] Int. Cl.[6] .................................................. A61B 17/32
[52] U.S. Cl. ............................. 606/167; 606/172; 30/293
[58] Field of Search .................................... 606/167, 172; 30/293, 294

[56] References Cited

U.S. PATENT DOCUMENTS

| | | | |
|---|---|---|---|
| 4,338,718 | 7/1982 | Olkkola | 30/171 |
| 4,647,300 | 3/1987 | Sheets . | |
| 4,672,964 | 6/1987 | Dee et al. . | |
| 4,730,613 | 3/1988 | Gordy . | |
| 4,759,363 | 7/1988 | Jensen . | |
| 4,791,928 | 12/1988 | Berke et al. . | |
| 4,815,218 | 3/1989 | Gordy . | |
| 4,823,790 | 4/1989 | Alperovich et al. . | |
| 4,862,890 | 9/1989 | Stasz et al. . | |
| 4,955,477 | 9/1990 | Bruno . | |
| 5,013,312 | 5/1991 | Parins et al. . | |
| 5,032,128 | 7/1991 | Alonso . | |
| 5,085,663 | 2/1992 | Tarr | 606/172 |
| 5,292,329 | 3/1994 | Werner . | |
| 5,324,299 | 6/1994 | Davison et al. . | |
| 5,441,512 | 8/1995 | Muller . | |

*Primary Examiner*—Michael Buiz
*Assistant Examiner*—David O. Reip
*Attorney, Agent, or Firm*—Bradley P. Heisler

[57] ABSTRACT

An incision device 10 is provided for precisely initiating and controlling the depth of an incision I in an artery A, such as a coronary artery A of a heart H, particularly while the heart H is beating. A handle 12 is provided for grasping by a surgeon and from which an arm 40 adjustably extends. A blade 70 is located at a free end 44 of the arm 40. A front depth control pin 80 and a rear depth control pin 90 are oriented parallel to each other and perpendicular to a plane in which the arm 40 and handle 12 are oriented and perpendicular to a cutting plane in which the cutting edge 74 of the blade 70 is oriented. The two depth control pins 80,90 together define a depth control plane with the cutting edge 74 of the blade 70 extending below the depth control plane to a desired maximum depth. The blade 70 is spaced sufficiently away from the front depth control pin 80 that the front depth control pin 80 can be located adjacent the artery A before the incision I is initiated. The incision device 10 can then be rotated, causing a tip 72 of the blase 70 to pierce the top wall T of the artery A while the front depth control pin 80 steadies the blade 70 and incision device 10, relative to the artery A in which the incision I is being made. Once the incision device 10 has been rotated until both the front depth control pin 80 and rear depth control pin 90 are adjacent the artery A, the incision I can be made to the desired length with the depth of the incision I maintained by the depth control pins 80,90.

17 Claims, 5 Drawing Sheets

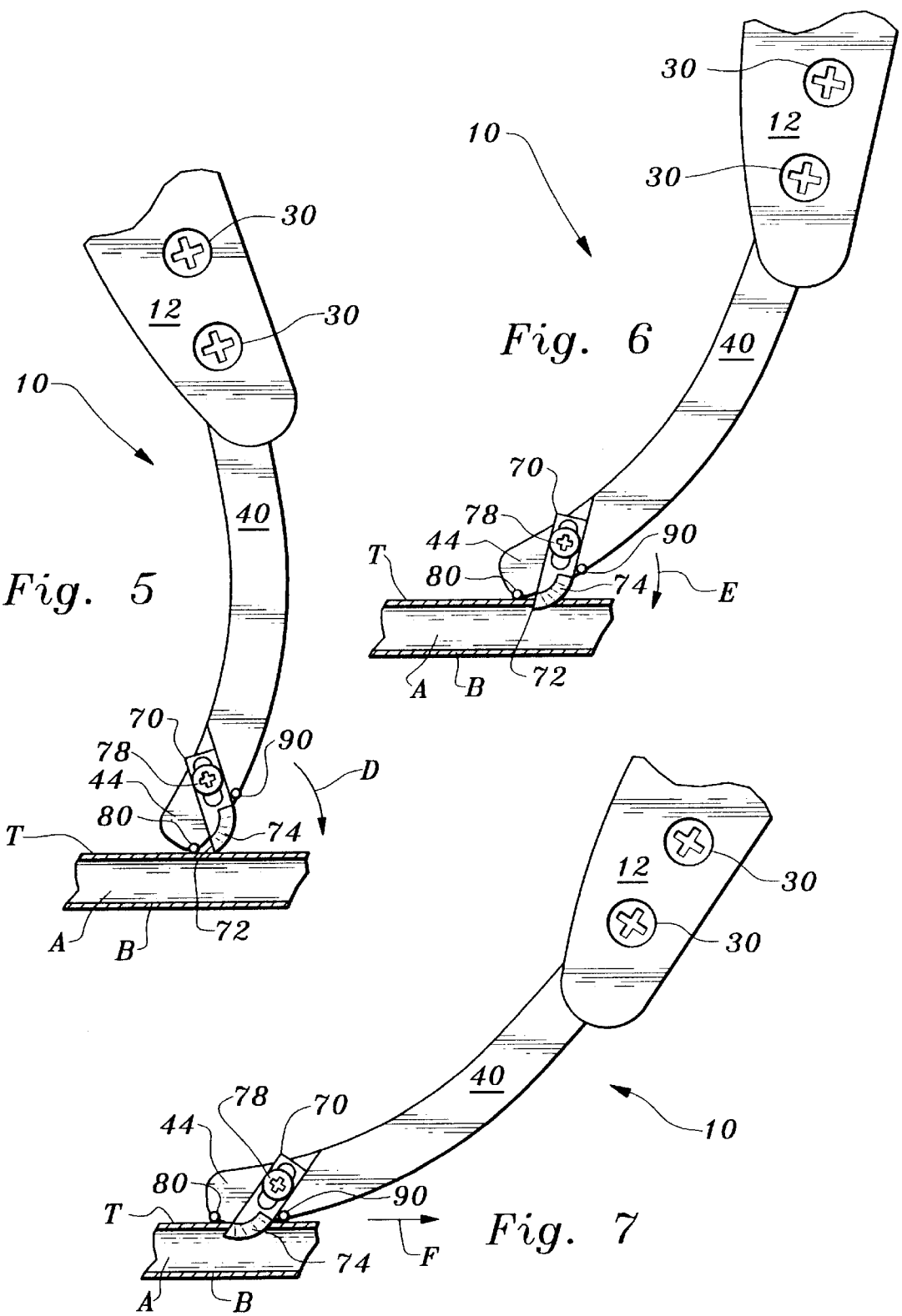

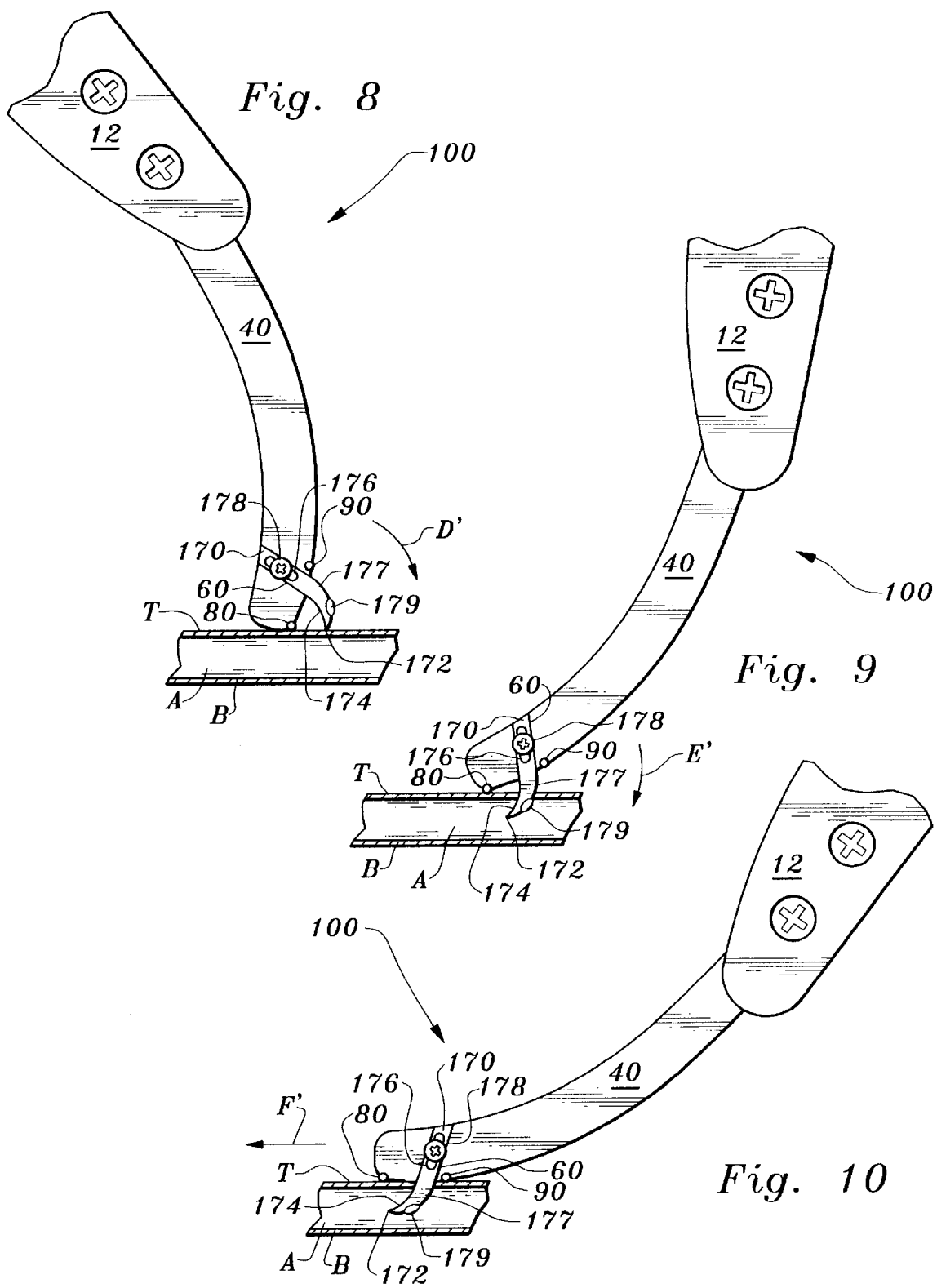

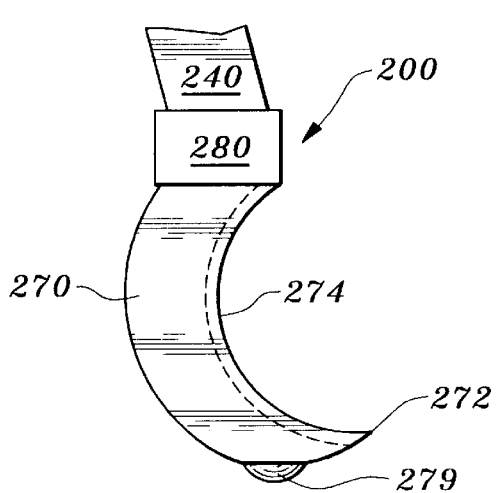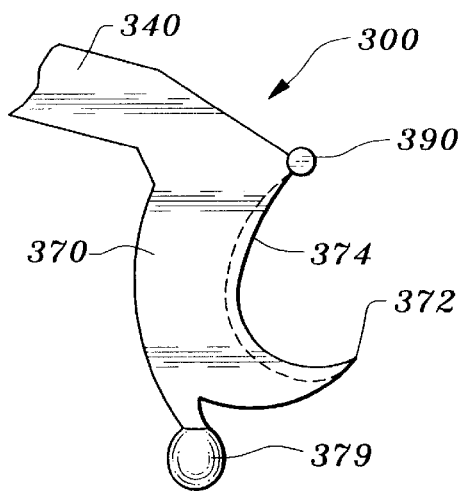
Fig. 13
Fig. 14
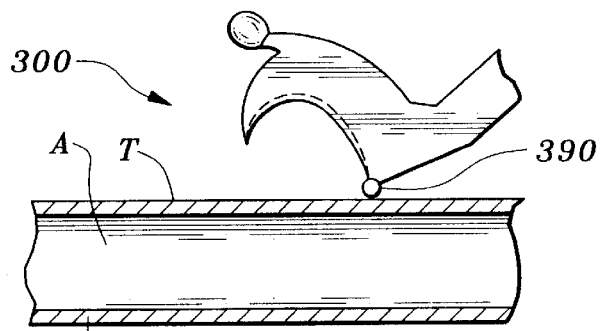
Fig. 15
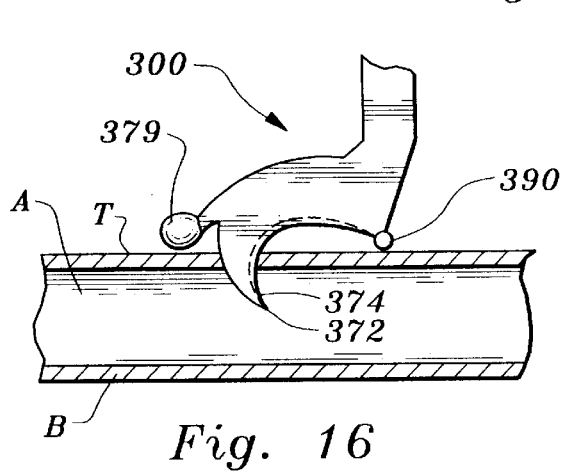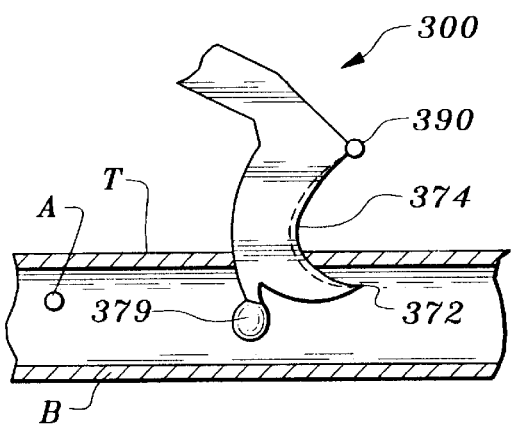
Fig. 16
Fig. 17

INCISION DEVICE

FIELD OF THE INVENTION

The following invention relates to incision devices for use in performing surgical procedures. More specifically, this invention relates to incision devices which are configured to precisely control the initiation of an incision and the depth of an incision.

BACKGROUND OF THE INVENTION

Scalpels and other incision devices are commonly used during surgical procedures to make incisions in body tissues including arteries and other body lumens. Incision devices come in a variety of different configurations to optimize their use for the type of incision and body tissue to be cut. One surgical procedure which requires a surgeon to make extremely precise incisions is coronary artery bypass graft surgery. During such "bypass" surgery, incisions are made in the coronary artery so that portions of the coronary artery which are blocked or otherwise damaged can be bypassed through an appropriate graft in the coronary artery where the incisions are made. Details of such bypass surgery are provided by reference to the paper: Direct Myocardial Revascularization by Saphenous Vein Graft in the Annuals of Thoracic Surgery, Vol. 10, No. 2, August, 1970 by Favaloro, et al.

In the past, such bypass surgery was only performed after the patient's heart was stopped from beating to allow the surgeon to precisely make the necessary incisions and place the graft. More recently however, surgeons have begun performing coronary bypass surgery of this type on a beating heart. Such beating heart bypass surgery, while beneficially decreasing the overall trauma to the patient during the procedure, is difficult to accurately perform. The surgeon must take care to make the incision as desired even while the patient's heart is beating and the coronary artery in which the incision must be made is in motion. The surgeon typically experiences greatest difficulty in initiating the incision in the coronary artery while the heart is beating. Secondarily, the surgeon has a difficult time maintaining accurate incision depth while completing the incision on the beating heart.

Accordingly, a need exists for an incision device which allows a surgeon to easily initiate an incision and maintain depth of an incision on a coronary artery even when the heart is beating. Similarly, in surgical procedures where a high level of incision accuracy is required and where incision initiation and depth control are critical, a need exists for incision devices which assist a surgeon in precisely initiating an incision and maintaining depth control for the incision.

Incision devices are known which provide some forms of depth control. For instance, the surgical scalpel taught by Gordy (U.S. Pat. No. 4,730,613) teaches a surgical scalpel having an extendible blade which features depth adjustment. However, surgical scalpels such as those taught by Gordy are not effective for use in maintaining incision depth for arterial incisions and other body lumen incisions and fail to assist a surgeon in initiating an incision at a precise location. Gordy teaches a foot adjacent the blade which is oriented in a plane substantially parallel to a cutting plane in which the blade is oriented. This is also the plane in which an artery in which an incision is to be made would be oriented when making arterial incisions such as those required for coronary artery bypass graft surgery. With surgical scalpels such as those taught by Gordy, the artery would be susceptible to sliding up between the two parallel elements forming the foot taught by Gordy and hence not accurately provide depth control as required for surgeries such as particularly coronary artery bypass graft surgery on a beating heart.

SUMMARY OF THE INVENTION

The incision device of this invention provides a blade attached to an arm extending from a handle which is graspable by a surgeon. The blade is fitted on the arm near a free end of the arm opposite the handle. A depth control member, such as a front depth control pin, is attached to the free end of the arm. This front depth control pin is oriented along a line perpendicular to a plane in which a cutting edge of the blade is oriented. The blade is spaced away from the depth control member a sufficient distance so that the depth control member can be located adjacent the coronary artery or other lumen to be cut first, with the blade spaced away from the artery and heart. When the heart beats, the artery and heart can only impact the depth control member, not the blade.

When the surgeon is ready for the incision to be initiated, the incision device is rotated until the cutting edge of the blade penetrates into the artery. The incision device can then be translated linearly along a length of the artery with the cutting edge of the blade making the desired incision in a top wall of the artery, while the depth control member rides along the top wall of the artery and controls the depth of the incision. A rear depth control pin can be provided parallel the front depth control pin and on an opposite side of the blade to further stabilize the incision device and precisely define a depth for the incision made by the blade of the incision device. If the heart beats while the incision is being made, the depth control pins keep the blade from cutting into a bottom wall of the artery and into the heart.

OBJECTS OF THE INVENTION

Accordingly, a primary object of the present invention is to provide an incision device which includes a depth control member which steadies the blade of the incision device adjacent an artery or other body lumen during initiation of an incision in that artery.

Another object of the present invention is to provide an incision device having a depth control member which defines an incision depth for a blade of the incision device during forming of an incision with the incision device.

Another object of the present invention is to provide an incision device which can be precisely positioned and utilized to form an incision in an artery even when the artery is moving, such as a coronary artery on a beating heart.

Another object of the present invention is to provide an incision device which includes means to prevent a blade of the incision device from cutting through a bottom wall of an artery while a top wall of the artery is being cut.

Another object of the present invention is to provide an incision device which can be utilized in surgical environments where little maneuvering room is provided for the incision device.

Another object of the present invention is to provide an incision device which can be adjusted to preselect a depth for the incision before utilizing the incision device.

Another object of the present invention is to provide a method for initiating and forming an incision in a lumen, such as an artery, in an accurate and reliable fashion even when the artery is in movement, such as the coronary artery of a beating heart.

Other further objects of the present invention will become apparent from a careful reading of the included description and claims and from a review of the included drawing figures.

BRIEF DESCRIPTION OF THE DRAWING FIGURES

FIGS. 5–7 are right side views of that which is shown in FIG. 1, revealing the three steps in initiating and forming an incision in an artery.

FIGS. 8–10 are right side views of an alternative embodiment of that which is shown in FIGS. 1–7, revealing the three steps in initiating and forming an incision utilizing the incision device shown therein.

FIG. 13 is a right side view of a blade portion of an alternative embodiment of that which is shown in FIG. 1, featuring a pad on the blade to prevent the blade from penetrating through a bottom wall of an artery.

FIG. 14 is a right side view of an alternative embodiment of that which is shown in FIG. 13, where a depth control pin and ball are provided to allow the incision device shown to initiate an incision and maintain accurate depth for the incision.

FIGS. 15–17 are right side views of that which is shown in FIG. 14 revealing the three steps involved in utilizing of the incision device shown therein to form an incision in a top wall of an artery.

DETAILED DESCRIPTION OF THE PREFERRED EMBODIMENT

Figure 1:
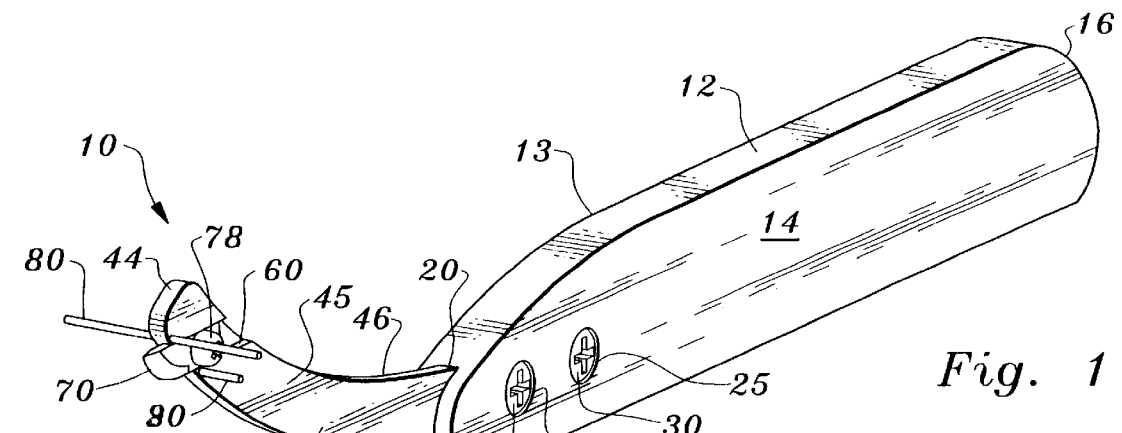
FIG. 1 is a perspective view of the incision device of this invention.
Figure 2:
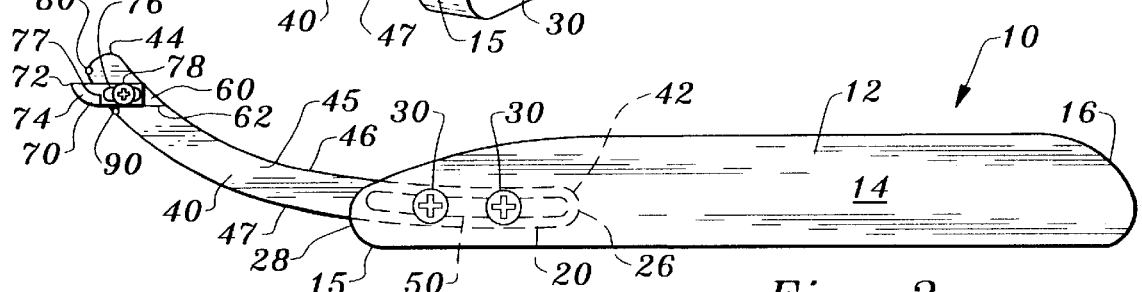
FIG. 2 is a right side view of that which is shown in FIG. 1.
Figure 3:
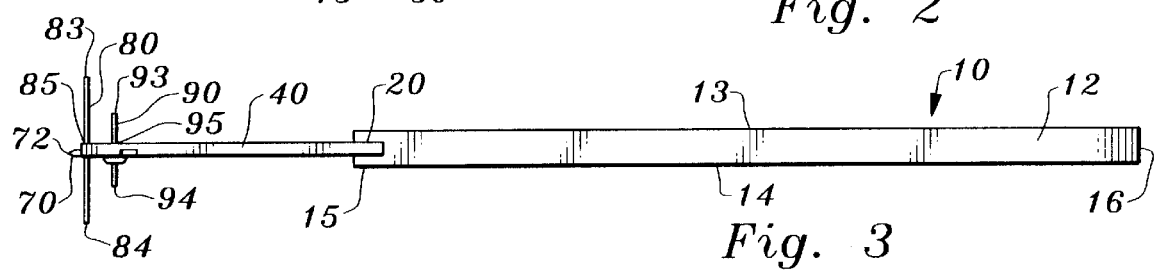
FIG. 3 is a top plan view of that which is shown in FIG. 1.
Figure 4:
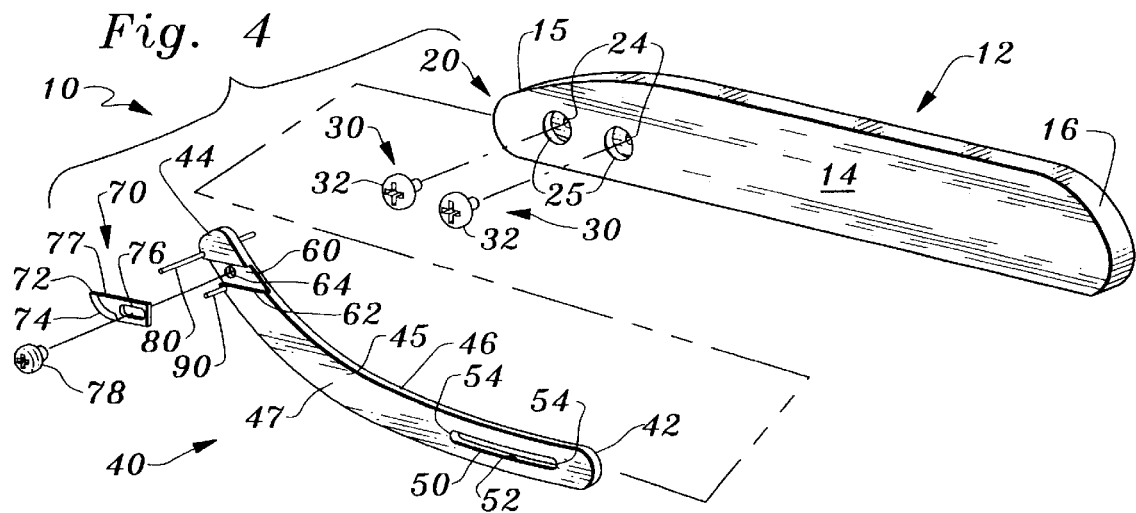
FIG. 4 is an exploded parts view of that which is shown in FIG. 1.

Referring to the drawings, wherein like reference numerals represent like parts throughout the various figures, reference numeral 10 is directed to an incision device for precisely initiating an incision I in an artery A (FIG. 11) and precisely maintaining a depth of the incision I. The incision device 10 is particularly useful in making incisions in a coronary artery A of a heart H while the heart H is still beating and the artery A is in motion.

In essence, and with particular reference to FIGS. 1–4, the incision device 10 includes a handle 12 with an arm 40 extending from the handle 12 and with a blade 70 attached to the arm 40. A front depth control pin 80 and a rear depth control pin 90 are attached to the arm 40 on either side of the blade 70. The depth control pins 80, 90 are oriented parallel to each other and perpendicular to a cutting plane in which a cutting edge 74 of the blade 70 is oriented. The front depth control pin 80 is spaced slightly away from the blade 70 so that the front depth control pin 80 can be placed adjacent a top wall T (FIGS. 5–7) of the artery A with the blade 70 above the top wall T. The incision device 10 is then rotated (along arrows D and E) until a tip 72 of the blade 70 pierces into the top wall T of the artery A. The two depth control pins 80, 90 can rest upon the top wall T of the artery A as the incision I (FIG. 11) is formed by moving the incision device 10 along arrow F (FIG. 7). The incision device 10 thus assists the surgeon in precisely initiating the incision I and in precisely controlling the depth of the incision I, even when the artery A is in motion.

More specifically, and with particular reference to FIGS. 1–4, specific structural details of the handle 12 and arm 40 of the incision device 10 are described. The primary purpose of the handle 12 and arm 40 are to provide a region on the incision device 10 for convenient and effective grasping by a hand of a surgeon. The arm 40 extends from the handle 12 to position the blade 70 in the desired position and orientation relative to the surgeon's hand for maximum effectiveness. While the configuration disclosed for the handle 12 and arm 40 are preferred to provide convenient and effective operation of the incision device 10, various different configurations for the handle 12 and arm 40 could be utilized to accommodate the particular preferences and needs of the surgeon.

In the preferred embodiment, the handle 12 is a rigid construct including a planar left surface 13 parallel to and spaced from a planar right surface 14. A front end 15 defines an end of the handle 12 closest to the arm 40 and a rear end 16 is located opposite the front end 15. Preferably, the handle 12 has its front end 15 and rear end 16 rounded so that the handle 12 can be comfortably held in a surgeon's hand without rough edges. A blind bore 20 passes into the handle 12 at the front end 15. The blind bore 20 provides a recess into which the arm 40 is attached. The blind bore 20 includes an open end 28 adjacent the front end 15 and a closed end 26 defining an innermost extent of the blind bore 20. Preferably, a contour of the blind bore 20 between the closed end 26 and open end 28 is substantially constant and has a cross-section generally matching that of the arm 40. Thus, the arm 40 is only allowed to telescope into and out of the blind bore 20, but is prevented from rotating or shifting within the blind bore 20.

Preferably, two threaded holes 24 are located in one side of the blind bore 20 (FIG. 4) with screw holes 25 oriented on an opposite side of the blind bore 20 and directly overlying each threaded hole 24. Arm screws 30 pass through the screw holes 25 and thread into the threaded holes 24. Each arm screw 30 has a head 32 with a diameter similar to a diameter of the screw holes 25. Thus, when the arm screws 30 are threaded into the threaded holes 24, the screw holes 25 are filled by the heads 32 of the arm screws 30.

The arm 40 is provided with an adjustment opening 50 which is basically an elongate slot passing through the arm 40 near an attached end 42 of the arm 40. The adjustment opening 50 has a width between inner surfaces 52 similar to a diameter of the arm screws 30. When the attached end 42 of the arm 40 is located within the blind bore 20, the arm screws 30 can be passed through the screw holes 25, through the adjustment opening 50 of the arm 40 and be threaded into the threaded holes 24. The head 32 of each arm screw 30 then impacts the arm 40 adjacent the adjustment opening 50 and securely attaches the arm 40 in fixed position relative to the handle 12.

Should fine adjustment of the arm 40 relative to the handle 12 be desired, the arm screws 30 can be loosened. The arm 40 can then be translated in and out of the blind bore 20 somewhat by allowing the arm screws 30 to move to different locations in the adjustment opening 50 in the arm 40. The adjustment opening 50 includes inner ends 54 which define a total length of the adjustment opening 50. When one of the arm screws 30 abuts one of the inner ends 54 of the adjustment opening 50, a maximum adjustability of the arm 40 is provided either defining a lengthiest configuration for the arm 40 and handle 12 or a most compact configuration for the arm 40 and handle 12. The arm screws 30 are tightened once the arm 40 is positioned where desired with respect to the handle 12, so that this desired orientation can be securely maintained during utilization of the incision device 10.

The arm 40 is formed from rigid material such as surgical steel and is formed to exhibit an elongate substantially constant cross-section. The arm 40 extends from the attached end 42 to a free end 44. The attached end 42 is preferably substantially linear adjacent the adjustment opening 50. However, a curve 45 is provided in the arm 40 between the attached end 42 and the free end 44. The curve 45 causes the free end 44 to be elevated slightly above the handle 12 when the handle 12 is oriented horizontally. The arm 40 includes a top surface 46 and a bottom surface 47 which maintain a constant distance between each other causing the arm 40 to have a constant width. The arm 40 is also substantially planar and aligned with a plane in which the cutting edge 74 of the blade 70 is oriented.

A groove 60 is formed in the arm 40 near the free end 44. The groove 60 is preferably located in only one side of the arm 40 and has a depth similar to a thickness of the blade 70. The groove 60 has two parallel spaced sides 62 which are spaced apart a distance similar to a width of the blade 70. A threaded hole 64 is oriented within the groove 60 and passes into the arm 40. The threaded hole 64 is utilized with a mounting screw 78 to attach the blade 70 to the arm 40 within the groove 60. The groove 60 provides a channel in which the blade 70 is restrained from rotation but which allows the blade 70 to slide to a desired position and then be secured to prevent further translation of the blade 70 relative to the arm 40.

With further reference to FIGS. 1–4, details of the free end 44 of the arm 40 and details of the blade 70 are further described. The blade 70 is preferably a rigid metallic construct formed from a material which can be sharpened, such as surgical steel. The blade 70 has a cutting edge 74 on one side thereof and a dull edge 77 opposite the cutting edge 74. A tip 72 defines an extremity of the blade 70 where the cutting edge 74 terminates. Preferably, the cutting edge 74 is swept into an arc and is oriented within a cutting plane. A mounting slot 76 passes through the blade 70 between the cutting edge 74 and the dull edge 77. To attach the blade 70 to the arm 40, a mounting screw 78 passes through the mounting slot 76 and is then threaded into the threaded hole 64 within the groove 60. The mounting slot 76 has a length greater than its width so that the blade 70 can be attached at a variety of different positions within the groove 60, causing the cutting edge 74 and tip 72 to extend a greater or lesser amount out of the groove 60 and away from the arm 40 depending on the particular desires of the surgeon.

As an alternative to the basic mounting screw 78 and mounting slot 76 configuration, various different blade 70 extension and retraction mechanisms can be utilized to more easily allow the surgeon to precisely adjust the distance that the blade 70 extends away from the arm 40. The tip 72 is preferably sharp along with the cutting edge 74 so that the tip 72 can pierce through body tissues, such as the top wall T of the artery A, when desired.

Two depth control pins, including a front depth control pin 80 and a rear depth control pin 90, are attached to the free end 44 of the arm 40 near the groove 60. Specifically, the front depth control pin 80 is preferably located adjacent the bottom surface 47 of the arm 40 at the extremity of the free end 44 of the arm 40, most distant from the handle 12. The front depth control pin 80 is preferably an elongate linear cylindrical construct having a left end 83 and a right end 84 defining ends of the front depth control pin 80 and a center 85 between the two ends 83, 84. The front depth control pin 80 is attached to the free end 44 of the arm 40 at the center 85 thereof.

The front depth control pin 80 is preferably oriented along a line perpendicular to the cutting plane of the blade 70 and perpendicular to a plane in which the arm 40 and handle 12 are located. The front depth control pin 80 is spaced from the groove 60 and from the blade 70 by a distance which is not greater than an overall diameter of the artery A in which the incision I is to be formed (FIGS. 5–7 and 11). The blade 70 is preferably oriented so that the front depth control pin 80 is on the side of the blade 70 closest to the dull edge 77.

The rear depth control pin 90 is an elongate linear cylindrical construct attached to the arm 40 along a line substantially perpendicular to the cutting plane of the blade 70 and perpendicular to the plane in which the arm 40 and handle 12 are oriented. The rear depth control pin 90 is located on a side of the groove 60 opposite the front depth control pin 80. The front depth control pin 80 and rear depth control pin 90 are preferably parallel to each other and reside within a common depth control plane. Preferably, no portions of the incision device 10 extend below this depth control plane except for the blade 70. The extent to which the blade 70 extends below this depth control plane is defined by the position which the blade 70 has within the groove 60, as defined when the mounting screw 70 is tightened through the mounting slot 76 in the blade 70.

Figure 11:
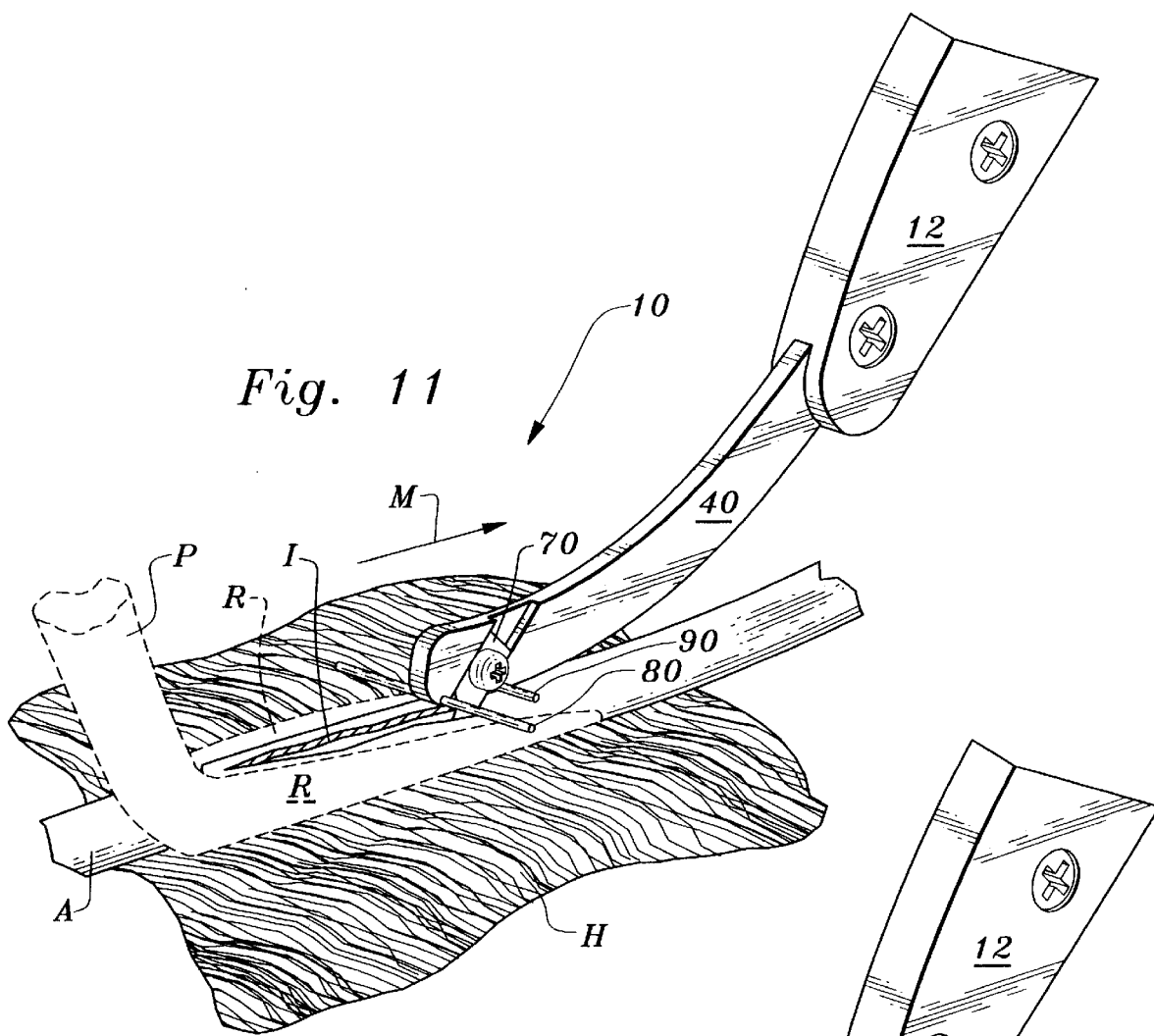
FIG. 11 is a perspective view of that which is shown in FIG. 1, in use forming an incision along with a pressure tool utilized to raise the artery and revealing how the artery is oriented adjacent a surface of the heart.
Figure 12:
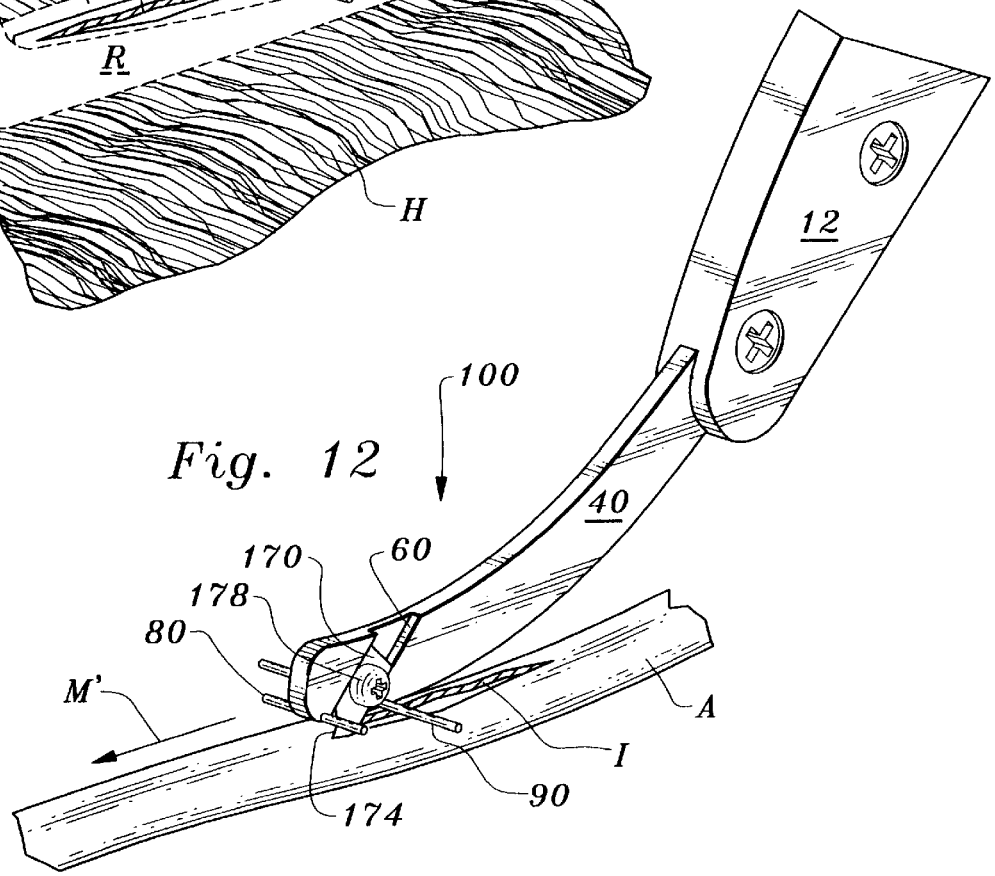
FIG. 12 is a perspective view of that which is shown in FIGS. 8–10, revealing how the incision device shown is utilized to form an incision in an artery.

Preferably, the blade 70 is oriented so that the cutting edge 74 and tip 72 of the blade 70 extend beyond the depth control plane a sufficient distance to pass entirely through the top wall T of the artery A, but not so far that any risk is provided that the blade 70 would impact the bottom wall B of the artery A. Preferably, the front depth control pin 80 is provided with a greater length than the length of the rear depth control pin 90. The front depth control pin 90 is provided with sufficient length that the front depth control pin 80 will be wider than the incision I and prevent the front depth control pin 80 from dropping into the incision I during formation of the incision I (FIG. 11).

For instance, in coronary artery surgery it has been found that making the front depth control pin 80 with a length of 0.8 inches and a diameter of 0.025 inches and making the rear depth control pin 90 with a length of 0.4 inches and a diameter of 0.025 inches has been effective. However, various different dimensions for the depth control pins 80, 90 could be selected to provide a desired operation depending on the particular use intended for the incision device 10.

In use and operation, and with particular reference to FIGS. 5–7 and 11, details of the use of the incision device 10 to initiate an incision I and to form an incision I are described. Initially, the user manipulates the arm screws 30 to provide the arm 40 in the desired position relative to the handle 12. The blade 70 can also have its position adjusted within the groove 60 of the arm 40 by adjusting the mounting screw 78. The blade 70 is adjusted to provide the blade 70 with a length beyond the depth control plane desired for the particular surgical procedure to be performed.

Once the surgical site has been appropriately prepared so that the heart H and coronary artery A are properly accessible and in position for forming of the incision I, the incision device 10 is located adjacent the artery A with the front depth control pin 80 adjacent the top wall T of the artery A and the tip 72 of the blade 70 just off of the top wall T of the artery A. Because the artery A may be in motion due to the beating of the heart H, the front depth control pin 80 prevents the tip 72 and cutting edge 74 of the blade 70 from accidentally cutting the artery A or other portions of the heart H adjacent the artery A should the incision device 10 be caused to accidentally be translated sideways along the front depth control pin 80. Rather, the front depth control pin 80 would merely be impacted against the artery A and heart H. Because the front depth control pin 80 is cylindrical and smooth in contour, no damage to the artery A or heart H is caused by having the front depth control pin 80 in contact with the artery A and heart H.

Once the surgeon is confident that the incision device 10 is in the correct position to initiate the incision I, with the front depth control pin adjacent the artery A, the incision device 10 is rotated, along arrow D of FIG. 5, causing the tip 72 of the blade 70 to impact the top wall T of the artery A. The incision device 10 is further rotated, along arrow E of FIG. 6, causing the tip 72 and cutting edge 74 of the blade 70 to cut into the top wall T of the artery A and through to an interior of the artery A. The incision device 10 is further rotated until the rear depth control pin 90 impacts the top wall T of the artery A (FIG. 7). The incision device 10 can then be translated linearly along a length of the artery A the desired distance, along arrow F of FIG. 7. When the incision I is complete, the incision device 10 is removed away from the artery A. Other steps in the surgical procedure can then be performed as is known in the art.

The front depth control pin 80 provides accurate positioning and steadying of the blade 70 of the incision device 10 immediately before the incision I (FIG. 11) is formed and during initiation of the incision I. Once the incision I has been initiated and the incision device 10 rotated until the rear depth control pin 90 is in position adjacent the top wall T of the artery A, the two depth control pins 80, 90 act together to control a depth of the blade 70, preventing the blade 70 from impacting the bottom wall B of the artery A and doing damage to the heart H or adjacent tissues. The coronary artery A is typically further held steady and raised up from the surface of the heart H by utilization of a pressure tool P (FIG. 11) which has two substantially parallel fingers R which can be oriented parallel to and on either side of the artery A. When the pressure tool P is pressed down against the surface of the heart H on either side of the artery A, the artery A tends to rise up between the fingers R a sufficient distance so that the top wall T of the artery A is above the fingers R and can be more easily accessed by the incision device 10 for forming of the incision I, as discussed above.

With particular reference to FIGS. 8–10 and 12, details of an alternative embodiment of the incision device 10, defining a forward cutting incision device 100, are provided. The forward cutting incision device 100 is substantially identical to the incision device 10 of the preferred embodiment except that a forward cutting blade 170 is fitted within the groove 60 of the preferred embodiment rather than the blade 70.

The forward cutting blade 170 is a rigid construct preferably formed from a metal such as surgical tool steel with a tip 172 at one end thereof and with a cutting edge 174 along one edge thereof and a dull edge 177 on an edge thereof opposite the cutting edge 174. A slot 176 passes through the blade and allows a screw 178 to adjustably secure the forward cutting blade 170 to the arm 40 within the groove 60 of the forward cutting incision device 100.

The primary difference between the forward cutting incision device 100 and incision device 10 of the preferred embodiment is that the forward cutting blade 170 is oriented with its cutting edge 174 closest to the front depth control pin 80, rather than as oriented with the incision device 10 of the preferred embodiment. Thus, the forward cutting incision device 100 is utilized by moving the incision device 100 toward the front depth control pin 80 in a forward direction (along arrow F' of FIG. 10), rather than towards the rear depth control pin 90 in a rearward direction (along arrow F of FIG. 7). In addition, the cutting edge 174 is concave so that the blade 170 has a tendency to remain below the top wall T of the artery A while an incision I (FIG. 12) is formed in the artery A. The dull edge 177 is also curved so that the blade 170 has a somewhat sickle-like configuration as it extends to the tip 172.

A pad 179 is preferably formed on the forward cutting blade 170 adjacent the dull edge 177. The pad 179 is preferably formed from a smooth material which can either be formed integrally with the forward cutting blade 170 or be a different material such as silicone or plastic. The pad 179 is particularly located at a lowermost portion of the forward cutting blade 170 when the depth control pins 80, 90 are both located adjacent the top wall T of the artery A.

The pad 179 provides a smooth surface against which the blade 70 can contact the bottom wall B, without cutting the bottom wall B. Because the pad 179 is below the tip 172, the pad 179 will impact the bottom wall B before the tip 172 is allowed to touch the bottom wall B and cause any damage to the bottom wall B, or the heart H beneath the bottom wall B. Thus, the pad 179 provides an added safety feature to prevent damage to the bottom wall B during forming of the incision I in the top wall T. While the pad 179 is shown with the forward cutting incision device 100, the pad 179 could similarly be provided with the incision device 10 of the preferred embodiment to similarly protect the bottom wall B of the artery A during cutting of the top wall T.

The forward cutting incision device 100 is utilized in a similar manner to the utilization of the incision device 10 of the preferred embodiment. As shown in FIGS. 8–10 and 12, the forward cutting incision device 100 is initially oriented with the front depth control pin 80 adjacent the top wall T with the blade 170 above the top wall T. The forward cutting incision device 100 is then rotated, along arrow D' until the tip 172 pierces the top wall T and passes into the artery A. The forward cutting incision device 100 is further rotated along arrow F' until both the front depth control pin 80 and rear depth control pin 90 are adjacent the top wall T of the artery A (FIG. 10). The forward cutting incision device 100 is then translated along arrow F' of FIG. 10, also arrow M' of FIG. 12, forming the incision I.

Preferably, the rear depth control pin 90 is provided with a greater length than the front depth control pin 80 and the rear depth control pin 90 has sufficient width to prevent the rear depth control pin 90 from dropping into the interior of the artery A. For instance, the rear depth control pin 90 of the forward cutting incision device 100 can have a length of 0.8 inches and the front depth control pin 80 of the forward cutting incision device 100 can have a length of 0.4 inches.

With particular reference to FIGS. 13 and 14, details of two other alternative embodiments of the incision device 10 of the preferred embodiment are provided. In FIG. 13 an alternative forward cutting incision device 200 is shown. The incision device 200 features a depth control block 280 which is oriented between an arm 240 corresponding to the arm 40 of the incision device 10 of the preferred embodiment with a blade 270 extending from the depth control block 280. The depth control block 280 is oriented perpen-

9 dicular to the plane in which the arm 240 and blade 270 reside and defines a maximum depth for the blade 270. The blade 270 is crescent shaped with a tip 272 opposite the depth control block 280. A cutting edge 274 defines a concave interior edge of the blade 270. A pad 279 is located near the tip 272 and on a side of the blade 270 opposite the cutting edge 274. The pad 279 provides a function similar to the pad 179 of the forward cutting incision device 100, while the depth control block 280 provides a similar function to that provided by the depth control pins 80, 90 of the incision device 10 of the preferred embodiment.

FIG. 14 shows a second alternative incision device 300. The incision device 300 has an arm 340 similar to the arm 240 of the first alternative forward cutting incision device 200. A blade 370 extends from the arm 340 and is generally crescent shaped. A tip 372 defines a maximum extent of the blade 370 away from the arm 340. A cutting edge 374 is located on a concave edge of the crescent shaped blade 370. A ball 379 is located on the blade 370 on a side thereof opposite the cutting edge 374 and near the tip 372. The ball 379 extends down below the blade 370 to provide greater clearance between the tip 372 and tissues below the tip 372 during utilization of the incision device 300. A rear depth control pin 390 is provided at an end of the cutting edge 374 opposite the tip 372.

The incision device 300 is utilized as shown in FIGS. 15–17. Initially, the incision device 300 is located adjacent an artery A which is to have its top wall T cut to form an incision. The arm 340 of the incision device 300 is angled so that the depth control pin 390 is adjacent the top wall T but the tip 372 is above the top wall T. The arm 340 of the incision device 300 is then rotated causing the tip 372 to pierce the top wall T of the artery A (FIG. 16). This initial penetration of the top wall T of the artery A is halted when the ball 379 impacts the top wall T.

The incision device 300 is then translated linearly parallel to the top wall T, allowing the cutting edge 374 to form the incision in the top wall T. Once the incision has begun to form, the ball 379 is allowed to drop beneath the top wall T and the incision device 300 is further rotated by lifting the depth control pin 390 up off of the top wall T, until the ball 379 forms a lowermost portion of the blade 370. The tip 372 remains below the top wall T and the incision is further formed with the cutting edge 374, while the tip 372 remains below the top wall T. Should the incision device 300 be translated too low into the artery A, such as by movement of the artery A associated with beating of the heart H (FIG. 11), the ball 379 may impact the bottom wall B but keep the tip 372 from damaging the bottom wall B. When the incision has been completely formed, the incision device 300 is elevated above the top wall T and away from the artery A.

Moreover, having thus described the invention, it should be apparent that various different modifications could be made to the incision device 10 of the preferred embodiment or the incision devices 100, 200, 300 identified as alternative embodiments herein. For instance, various different dimensions for the structures of the incision devices 10, 100, 200, 300 could be utilized so that the incision devices will have optimal configurations for use with various different arteries or other body lumens or other body tissues in which incisions are to be formed. Additionally, while the use of the incision devices 10, 100, 200, 300 are described with respect to the formation of an incision in a coronary artery A of a heart H, during surgery on a beating heart H, the incision devices 10, 100, 200, 300 could similarly be utilized for a variety of other incisions where precise depth control and ease in precisely initiating the incision is of particular importance.

10

What is claimed is:

1. An incision device for making incisions of uniform depth on a beating heart, the device comprising in combination:

a handle;

a blade in fixed position relative to said handle, said blade including at least one cutting edge oriented within a cutting plane;

a depth control member located in position intersecting said cutting plane in an orientation substantially perpendicular to said cutting plane;

said depth control member intersecting said cutting plane at a position spaced from said blade tip by an amount equivalent to a preselected cutting depth, such that when said incision device is located with said depth control member abutting tissues being cut, said cutting edge does not cut into the tissues beyond the preselected cutting depth; and wherein said depth control member includes a depth control pin oriented perpendicular to an elongate arm attached to said handle, said blade attached to said arm, said arm oriented parallel to said cutting plane.

2. The incision device of claim 1 wherein said blade includes a sharp tip defining one end of said cutting edge.

3. The incision device of claim 1 wherein said blade includes a blunted surface within said cutting plane and on a portion of said cutting edge most distant from said depth control member, said blunt surface being sufficiently blunt to prevent cutting of tissues passing adjacent said blunt surface.

4. The incision device of claim 1 wherein said blade is adjustably attached to said arm through a cutting depth adjustment means, said cutting depth adjustment means adjusting a distance between said cutting edge and said depth control pin.

5. The incision device of claim 4 wherein said blade depth adjustment means includes a linear groove in said arm having a width similar to a width of said blade, said groove located at an end of said arm opposite said handle, said groove including means to secure said blade at multiple positions within said groove.

6. The incision device of claim 1 wherein a second pin extends perpendicularly from said arm and parallel to said depth control pin, said depth control pin and said second pin together defining a depth control plane perpendicular to said cutting plane.

7. The incision device of claim 6 wherein said second pin is located on a side of said blade opposite said depth control pin, said cutting edge of said blade located on a side of said blade closest to said depth control pin.

8. The incision device of claim 6 wherein said second pin is located on a side of said blade opposite said depth control pin, said cutting edge of said blade located on a side of said blade closest to said second pin.

9. The incision device of claim 8 wherein said depth control pin is longer than said second pin.

10. A method for precisely and accurately making an incision on a beating heart, including the steps of:

providing an incision device including a handle, a blade fixed in position relative to the handle, the blade including at least one cutting edge oriented within a cutting plane, a depth control member located in a position intersecting said cutting plane in an orientation substantially perpendicular to said cutting plane, said depth control member intersecting said cutting plant at a position spaced from said blade tip by an amount equivalent to a desired cutting depth, such that when said incision device is located with said depth control member abutting tissues being cut, said cutting edge does not cut into the tissues beyond the desired cutting depth;

placing the incision device adjacent a tissue on the beating heart to be cut with the depth control member abutting a surface of the beating heart with the cutting edge of the incision device above the tissue to be cut;

moving the handle downward until the cutting surface impacts and cuts into the tissue to be cut; and translating the handle and attached blade in a desired direction while keeping the depth control member adjacent the surface of the beating heart.

11. The method of claim 10 including the further steps of:

preselecting a depth for the incision to be made into the tissues of the beating heart;

adjusting a distance between the cutting edge of the blade and the depth control member to match the preselected depth; and fixing the blade in position relative to the depth control member.

12. The method of claim 11 including the further steps of:

configuring the depth control member as a depth control pin oriented perpendicular to the cutting plane; and providing a second pin parallel to the depth control pin and on a side of the blade opposite the depth control pin, the second pin and the depth control pin together defining a depth control plane perpendicular to the cutting plane.

13. The method of claim 12 including the further step of locating the cutting edge on a side of the blade closer to the second pin than to the depth control pin.

14. The method of claim 12 including the further step of locating the cutting edge on a side of the blade closer to the depth control pin than to the second pin.

15. The method of claim 14 including the further step of providing the cutting edge of the blade with a blunt pad at a position on the cutting edge most distant from the depth control pin, such that the pad can ride along a bottom wall of an artery while the incision device is cutting a top wall of the artery located adjacent the depth control plane while the incision device is translated according to said translating step.

16. An incision device for accurately and precisely making incisions in a body lumen such as an artery on a beating heart, the device comprising in combination:

a handle adapted to be gripped by a surgeon;

an arm attached to said handle and extending from said handle;

a blade attached to said arm and extending from said arm to a tip, said blade including a cutting edge, said tip and said cutting edge oriented within a cutting plane;

a means to control a depth that said cutting edge penetrates into an artery, such that penetration of the cutting edge through a bottom wall of the artery adjacent the beating heart is avoided;

wherein said depth control means includes at least one depth control member located in position intersecting said cutting plane in an orientation substantially perpendicular to said cutting plane, said depth control member intersecting said cutting plane at a position spaced from said blade tip by an amount equivalent to a preselected cutting depth and less than a distance between a top wall of the artery and the bottom wall of the artery, such that when said incision device is located with said depth control member abutting the top wall of the artery, the cutting edge does not cut into the bottom wall of the artery; and wherein said depth control member is a depth control pin fixed perpendicular to said arm on a side of said blade opposite said handle.

17. The incision device of claim 16 wherein said means to control depth includes a second pin parallel to said depth control pin and located on a side of said blade opposite said depth control pin, said depth control pin and said second pin together defining a depth control plane perpendicular to said cutting plane in which said cutting edge is located, said tip of said blade extending away from said depth control plane to a depth less than a distance between the top wall of the artery and the bottom wall of the artery and to a depth greater than a thickness of the top wall of the artery.

* * * * *